United States Patent
Abe et al.

(10) Patent No.: US 6,843,199 B2
(45) Date of Patent: Jan. 18, 2005

(54) HEAT-SENSITIVE ODOR-EMITTING COMPONENT

(75) Inventors: Tomiya Abe, Tokyo (JP); Hiroshi Kasugai, Tokyo (JP); Hiroshi Kamoshida, Tokyo (JP); Shigeru Kashiwazaki, Tokyo (JP)

(73) Assignee: Hitachi Cable, Ltd., Tokyo (JP)

( * ) Notice: Subject to any disclaimer, the term of this patent is extended or adjusted under 35 U.S.C. 154(b) by 0 days.

(21) Appl. No.: 10/242,670

(22) Filed: Sep. 13, 2002

(65) Prior Publication Data

US 2004/0049983 A1 Mar. 18, 2004

(51) Int. Cl.$^7$ .............................. G01D 21/00; G01K 1/12
(52) U.S. Cl. .................... 116/106; 116/207; 116/214; 116/216; 239/71; 239/75
(58) Field of Search .................... 116/101, 106, 116/201, 207, 214, 216–219; 239/57, 60, 71, 75; 424/76.1–76.4

(56) References Cited

U.S. PATENT DOCUMENTS

| 1,755,642 A | * | 4/1930 | Gannon | 116/214 |
| 3,479,983 A | * | 11/1969 | Brot et al. | 116/214 |
| 4,773,350 A | * | 9/1988 | Lyons | 116/214 |
| 5,188,909 A | * | 2/1993 | Pedicini | 429/7 |
| 5,898,356 A | * | 4/1999 | Gascoyne et al. | 337/15 |

FOREIGN PATENT DOCUMENTS

| JP | 63-111434 A | 5/1988 |
| JP | 63-111435 A | 5/1988 |
| JP | 64-53930 U | 4/1989 |
| JP | 5-018831 | 1/1993 |
| JP | 6-066646 | 3/1994 |
| JP | 6-066647 | 3/1994 |

* cited by examiner

Primary Examiner—John J. Vrablik
(74) Attorney, Agent, or Firm—Foley & Lardner LLP

(57) ABSTRACT

An odor-emitting port is provided in a housing member composed mainly of an inorganic material. An odorous material is contained in the housing member, and the odor-emitting port is sealed with a low-melting metal to constitute a heat-sensitive odor-emitting component. In this heat-sensitive odor-emitting component, as soon as the temperature of a heat generation site has reached a predetermined value, the low-melting metal is instantaneously melted down to open the odor-emitting port through which the odorous material contained in the housing member is immediately spread around the odor-emitting component. Therefore, the odor-emitting component is highly sensitive to temperature. Further, since the housing member is formed of an inorganic material, the long-term stability can be improved.

18 Claims, 6 Drawing Sheets

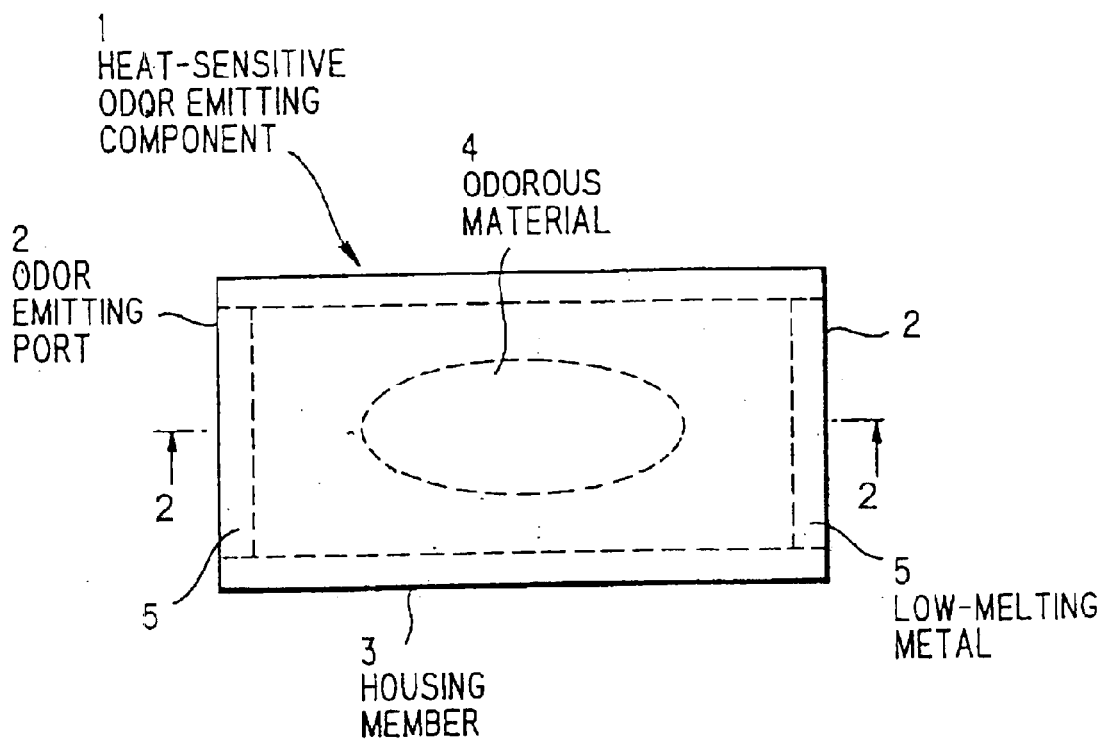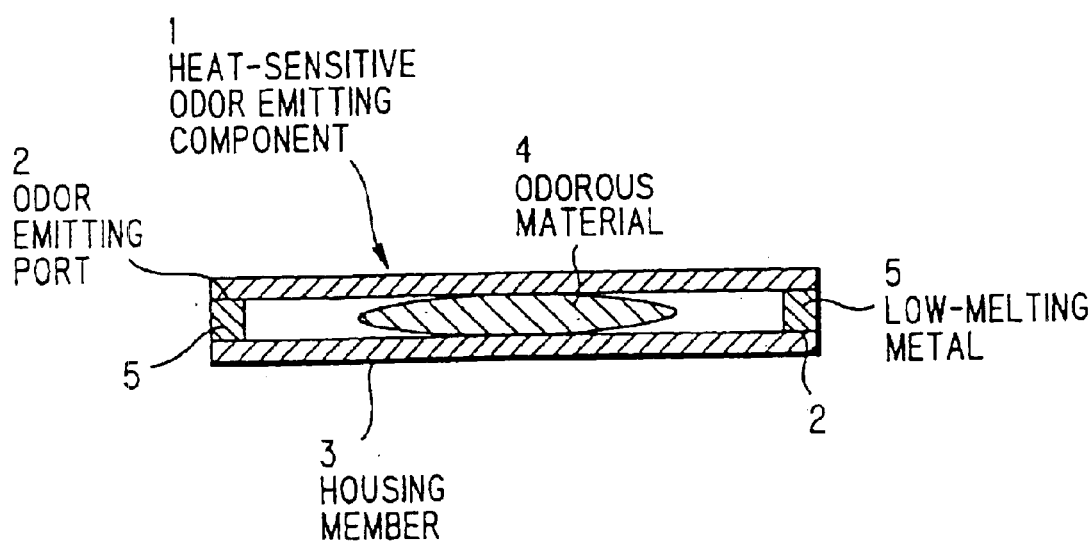

FIG. 10
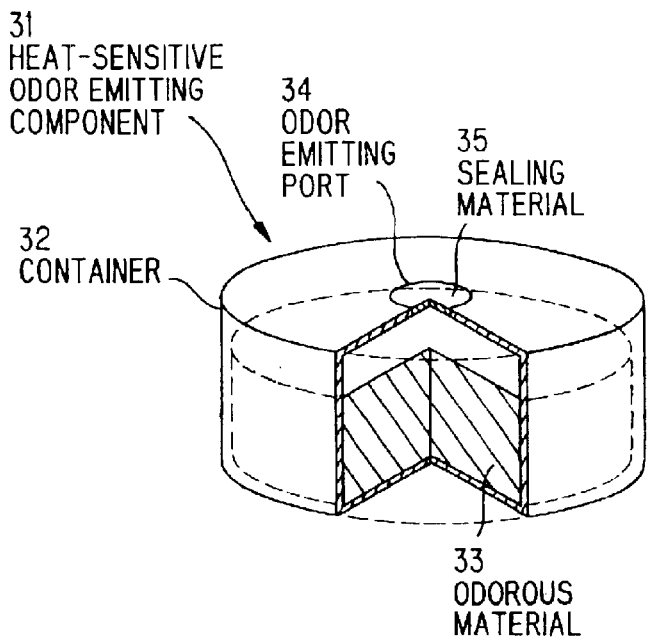
FIG. 11A  FIG. 11B
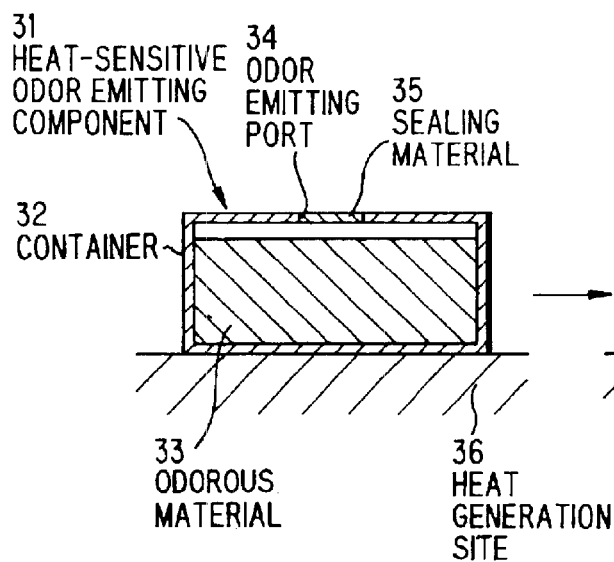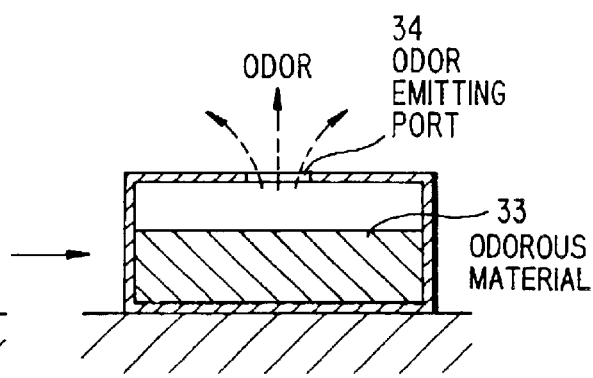

HEAT-SENSITIVE ODOR-EMITTING COMPONENT

BACKGROUND OF THE INVENTION

1. Field of the Invention

The invention relates to a heat-sensitive odor-emitting component which emits an odorous material upon a rise in temperature.

2. Prior Art

In conventional electric equipment, domestic equipment, and other equipment, for example, an increase in load, a contact failure, or leakage of electricity causes the flow of overcurrent which extremely increases the temperature of the equipment. This is causative of a fault or sometimes leads to a great overheating accident such as a fire.

In an example of a method for preventing the overheating accident, a color change tape, which causes a change in color upon a rise in temperature, is previously applied to a site where heat generation is expected, and whether or not the color has been changed is viewed to detect the abnormal heat generation phenomenon. This method is disadvantageous in that there is a need to always monitor the color-change tape and a local overheating phenomenon within the equipment cannot be accurately grasped.

Further, a method is also considered wherein an electric thermal resistance-type thermal sensor or the like is previously mounted on a site where heat generation is expected and the occurrence of an abnormal heat generation phenomenon is learned, for example, by an alarm. This thermal sensor is generally expensive and, in addition, a large number of thermal sensors, wiring, and alarm equipment should be mounted together. This is not practical from the viewpoint of cost.

For overcoming this disadvantage, a method has been proposed wherein an odor-emitting material, such as an alcohol, is sealed into a resin capsule, a resin tape, or a resin tube and this is previously mounted on a site where heat generation is expected. In this method, upon heat generation, the capsule or the like, into which the odor-emitting material has been sealed, is melted, and the odor-emitting material present inside the capsule or the like is emitted. As a result, the presence or absence of the odor is perceived by a person near the equipment either directly or indirectly by means of a gas detector or the like to detect the occurrence of the abnormal overheating phenomenon (for example, Japanese Patent Laid-Open Nos. 18831/1993, 66646/1994, and 66647/1994).

In the above conventional odor-emitting capsule, an odor-emitting material has been sealed into a resin capsule, tape, or tube. Since the resin (polymeric material) for forming the capsule, tape or the like is generally larger in specific heat and melting temperature width as compared with inorganic materials such as metals, the temperature working accuracy is low. As a result, there is a fear that the odor-emitting material does not work even when the temperature has reached the abnormal overheating temperature region, or otherwise the odor-emitting material works before the temperature reaches the abnormal overheating temperature region. Further, the durability and adhesion to heat generation site of the resin material are so low that long-term stability is also disadvantageously poor.

In addition, the abnormal overheating temperature at a site as an monitoring object varies depending upon the type of the equipment and the like. In the construction of the conventional odor-emitting capsule, it is difficult to control the operating temperature with high accuracy.

SUMMARY OF THE INVENTION

The invention has been made with a view to effectively solving the above problems of the prior art, and it is an object of the invention to provide a novel heat-sensitive odor-emitting component which possesses high sensitivity to heat and, at the same time, possesses excellent long-term stability.

It is another object of the invention to provide a novel heat-sensitive odor-emitting component which possesses high sensitivity to heat and excellent long-term stability and is also highly stable and reliable for shortcircuiting accidents.

It is a further object of the invention to provide a novel heat-sensitive odor-emitting component which is less likely to cause erroneous working and can surely notify of the occurrence of an abnormal overheating phenomenon.

According to the first feature of the invention, a heat-sensitive odor-emitting component comprising: a housing member composed mainly of an inorganic material; at least one odor-emitting port provided in the housing member; and an odorous material contained in the housing member, the odor-emitting port having been sealed with a low-melting metal.

In the heat-sensitive odor-emitting component according to the first feature of the invention, unlike the prior art technique wherein the housing member containing an odorous material per se is melted to emit the odorous material contained in the housing member, an odor-emitting port is previously provided in the housing member and is sealed with a low-melting metal, and the odor-emitting port is opened by the melting of the low-melting metal to emit the odorous material contained in the housing member.

Since the odor-emitting port is sealed with the low-melting metal having lower specific heat and smaller melting temperature width than a resin, as soon as the temperature has reached a predetermined temperature, the low-melting metal is instantaneously melted to release the odorous material from the inside of the housing member. Thus, the heat-sensitive odor-emitting component is highly sensitive to temperature.

The housing member is formed of a material composed mainly of an inorganic material. Specifically, the housing member may be formed of a metal foil, a composite film of a metal foil stacked on a polymeric film, glass, a glass-coated polymeric film, or a metallic container. In this case, as compared with resin, the housing member formed of the above material is not deteriorated over a long period of time, and stable function can be realized, that is, erroneous working attributable, for example, to the leakage of the odorous material caused, for example, by deterioration or breakage can be avoided.

Further, coating an adhesive onto the surface of the housing member to fix the housing member to a heat generation portion permits the housing member to be firmly adhered and mounted onto an optimal position independently of the heat generation site, shape and the like.

According to the second feature of the invention, a heat-sensitive odor-emitting component comprises: a metallic container; at least one odor-emitting port provided in the metallic container; an odorous material contained in the metallic container; a low-melting metallic lid for sealing the odor-emitting port; and an electrically insulating layer covering the circumference of the metallic container.

According to the above construction, even when a short-circuiting accident has occurred, no electricity flows across the metallic container. Therefore, troubles such as the melting of the lid or the leakage of the odorous material contained in the container can be surely avoided.

When an electrically insulting coating material is used for the formation of the electrically insulating layer, the electrically insulating layer can be easily formed on the surface of the metallic container to cover the metallic container.

When the lid is formed of a low-melting lead-free alloy, the melting of the lid does not have any adverse effect on human and environment around the odor-emitting component.

The odorous material is preferably ethyl alcohol or an aqueous ethyl alcohol solution.

According to the third feature of the invention, a heat sensitive odor-emitting component comprises: a container; at least one odor-emitting port provided in the container; and an odorous material contained in the container, the odor-emitting port having been sealed with a sealant which melts at a predetermined temperature to open the odor-emitting port, the difference between the melting point of the sealant and the boiling point of the odorous material being within ±20° C.

The above construction can avoid troubles including that the odor-emitting component erroneously works before the temperature reaches an abnormal overheat temperature, or the odor-emitting component erroneously does not work even after the temperature reaches an abnormal overheat temperature.

Further, the odor-emitting component can surely advise of the occurrence of an abnormal overheated phenomenon.

The odorous material may be a combustible material.

The sealant is preferably formed of an alloy having a lower melting point than the container.

Preferably, the low-melting alloy has a melting point of 60 to 180° C.

The low-melting alloy is preferably an indium-tin alloy, a tin-bismuth alloy, an indium-bismuth alloy, or an indium-tin-bismuth alloy.

The low-melting alloy is more preferably an indium-tin alloy comprised of indium and tin at a weight ratio of 34:66, a tin-bismuth alloy comprised of tin and bismuth at a weight ratio of 48:52, an indium-bismuth alloy comprised of indium and bismuth at a weight ratio of 58:42, or an indium-tin-bismuth alloy comprised of indium, tin, and bismuth at a weight ratio of 48.2:44.4:7.4.

BRIEF DESCRIPTION OF THE DRAWINGS

The invention will be explained in more detail in conjunction with the appended drawings, wherein:

FIG. 1 is a plan view showing a preferred embodiment of the heat-sensitive odor-emitting component according to the first feature of the invention;

FIG. 2 is a cross-sectional view taken on line 2—2 of FIG. 1;

FIG. 5 is a diagram showing another preferred embodiment of the heat-sensitive odor-emitting component according to the first feature of the invention, wherein

FIG. 10 is a partially broken perspective view showing a preferred embodiment of the heat-sensitive odor-emitting component according to the third feature of the invention; and FIG. 11 is a diagram illustrating mounting and operation of the heat-sensitive odor-emitting component according to the third feature of the invention, wherein FIG. 11A is a cross-sectional view showing the state of the heat-sensitive odor-emitting component according to the third feature of the invention mounted on a heat generation site and FIG. 11B a conceptual diagram showing the state of operation of the heat-sensitive odor-emitting component according to the third feature of the invention.

DESCRIPTION OF THE PREFERRED EMBODIMENTS

Figure 3:
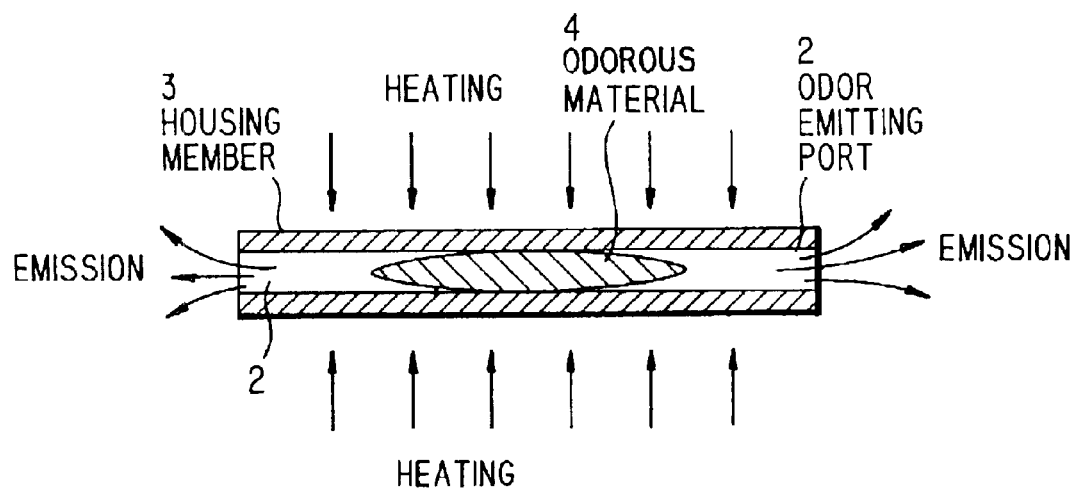
FIG. 3 is a conceptual diagram showing the function of the heat-sensitive odor-emitting component according to the first feature of the invention.

Preferred embodiments of the invention will be explained in conjunction with the accompanying drawings.

First Feature of the Invention

Preferred embodiments of the heat-sensitive odor-emitting component according to the first feature of the invention will be explained in conjunction with FIGS. 1 to 7.

FIGS. 1 and 2 show a preferred embodiment of the heat-sensitive odor-emitting component 1 according to the first feature of the invention.

As shown in the drawings, in this heat-sensitive odor-emitting component 1, an odorous material 4 is contained in a housing member 3 in a flat box form having odor-emitting ports 2, 2 on its respective both ends. The odor-emitting ports 2, 2 are closed with a low-melting metal 5, 5 to seal the odorous material 4 into the housing member 3.

Here, for the housing member 3, the material and shape thereof are not particularly limited so far as the material is composed mainly of an inorganic material, that is, at least has a melting point above the low-melting metal 5, 5 and, at the same time, has corrosion resistance high enough to avoid the leakage of the odorous material 4 contained in the housing member 3 for a long period of time. More specifically, the material may be a single inorganic material, such as a metal or glass, a composite film formed of a metal foil and a polymeric film, or a composite film formed of glass and a polymeric film, or the like. For the shape of the housing member 3, in addition to the flat box form as shown in the drawing, a container form, a cylindrical (tubular) form, or a bag form produced by laminating sheet materials on top of each other or one another may also be adopted.

The low-melting metal 5 for sealing the odor-emitting ports 2, 2 of the housing member 3 is not particularly limited so far as the metal has a melting point in a temperature region just below a temperature which possibly leads to accidents caused by overheating, troubles of equipment caused by overheating, and the like, for example, has a melting point in the range of 50 to 200° C. Specifically, metals, such as lead, tin, zinc, bismuth, and indium, or alloys of these metals are suitable, and a desired melting temperature can be freely set by selecting a metal from these metals or alloying these metals at a predetermined ratio. For example, indium per se has a melting point of about 156° C., and tin per se has a melting point of 232° C. On the other hand, alloying 52 parts by weight of indium with 48 parts by weight of tin provides a low-melting alloy having a melting point of 117° C. This indium-tin alloy is used for a heat generation site where a rise in temperature to above the temperature 117° C. possibly leads to accidents caused by overheating or troubles caused by overheating. The use of harmful metals, such as lead, is preferably avoided from the viewpoint of environmental contamination.

The odorous material 4 is not particularly limited so far as the material is solid or liquid at room temperature and, upon heating, can be volatilized and detected, for example, by the sense of smell of human or a gas detection sensor. Examples of odorous materials usable herein include: alcohols such as ethanol, propanol, butanol, and phenol; saturated hydrocarbons such as methane, butane, and octane; unsaturated hydrocarbons such as ethylene, acetylene, butadiene, benzene, and naphthalene; ketones such as acetone, and methyl ethyl ketone; carboxylic acids such as formic acid, acetic acid, lactic acid, acrylic acid, and methacrylic acid; and esters such as methyl acetate and ethyl acetate.

Figure 4:
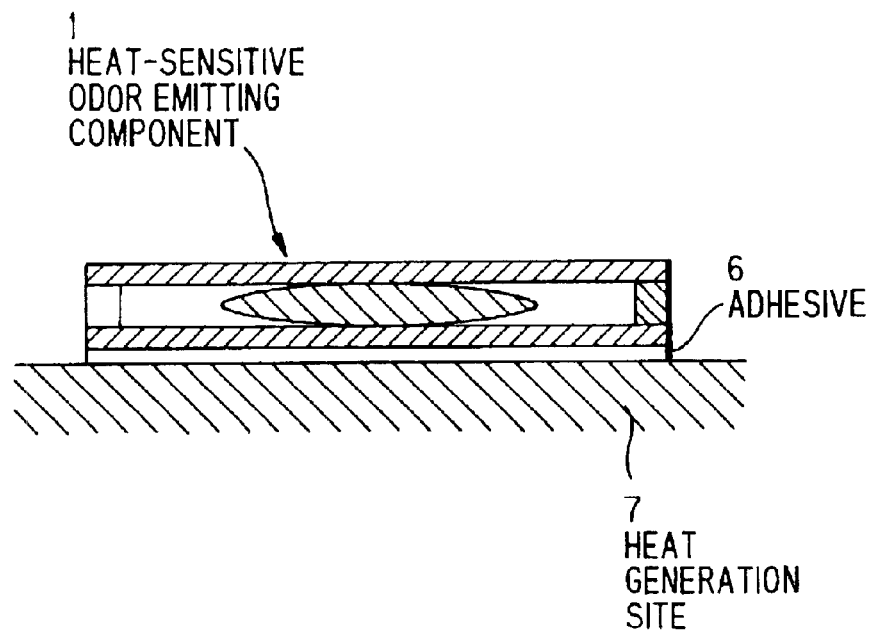
FIG. 4 is a conceptual diagram illustrating the state of the heat-sensitive odor-emitting component according to the first feature of the invention mounted on a heat generation site.

The heat-sensitive odor-emitting component 1 according to the invention having the above construction is installed around a beat generation site as a monitoring object, for example, a motor, an integrated circuit, or a distribution board, or may be applied and fixed directly to the heat generation site 7 with the aid of an adhesive 6 as shown in FIG. 4. In this case, when the temperature of the heat generation site 7 is generally raised to above the operation temperature and is consequently brought to an overheated state, as shown in FIG. 3, the heat immediately melts down the low-melting metal 5 which seals the odor-emitting ports 2, 2 of the housing member 3. As a result, the odor-emitting ports 2, 2 are instantaneously opened, and the odorous material 4 contained in the housing member is emitted at a time to the outside of the housing member.

This permits a person near the order-emitting component to perceive the occurrence of the phenomenon by the sense of smell of the person. Alternatively, the presence of the odorous material 4 may be detected by a gas detection sensor which then sounds the alarm or carries out other means to advise the person of the overheating. Thus, the person can be surely learned directly or indirectly the fact that the heat generation site 7 as the monitoring object is in an overheated state and has a fear of the overheating causing an accident.

Thus, unlike the conventional heat-sensitive odor-emitting component wherein the resin microcapsule, film or the like having an odorous material housed therein per se is melted or broken to emit the odorous material, in the heat-sensitive odor-emitting component 1 according to the first feature of the invention, the odor-emitting ports 2 for emitting the odorous material 4 are provided in the housing member 3 and the odor-emitting ports 2 are sealed with a low-melting metal 5 which has lower specific heat and smaller melting temperature width as compared with the resin. Therefore, in the heat-sensitive odor-emitting component according to the first feature of the invention, at the same time that the temperature of the heat generation site 7 or around the heat generation site 7 reaches a predetermined temperature, the low-melting metal 5 is melted down at a time, and the odor-emitting ports 2 are instantaneously opened. As a result, the odorous material contained within the housing member is immediately released around the odor-emitting component. Thus, the heat-sensitive odor-emitting component according to the first feature of the invention has a high sensitivity to temperature.

Further, unlike the prior art technique, the housing member 3 for housing therein the odorous material 4 per se has no need to be melted and thus may be formed of a material composed mainly of an inorganic material such as a metal or glass. Therefore, as compared with the resin, the housing member per se is less likely to be deteriorated and thus is highly stable for a long period of time.

Figure 5A:
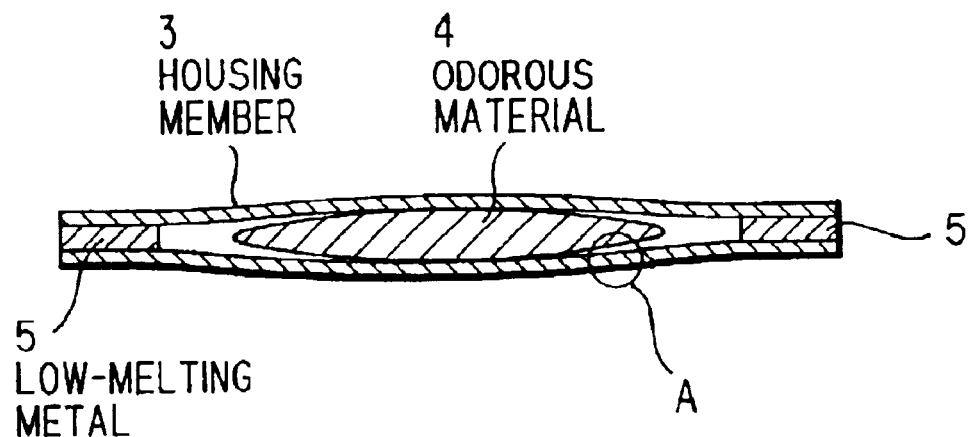
FIG. 5A is a cross-sectional view of the heat-sensitive odor-emitting component and FIG. 5B a partially enlarged diagram showing part A in FIG. 5A.
Figure 5B:
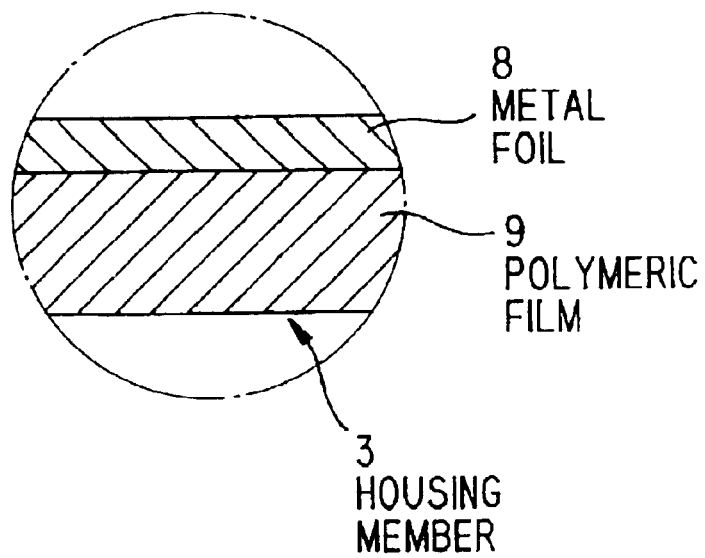
Figure 6:
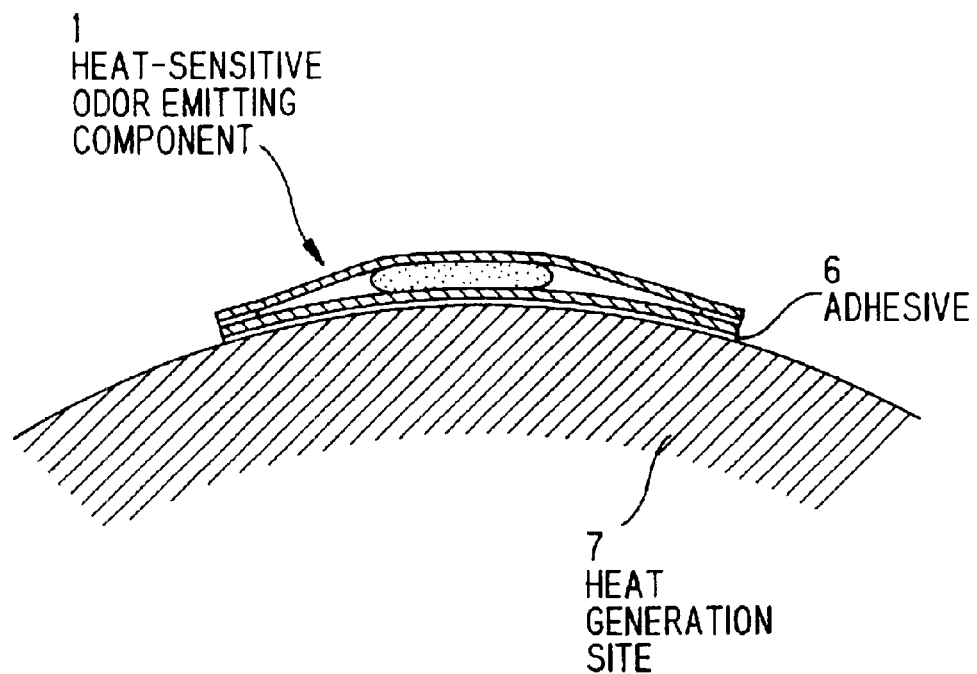
FIG. 6 is a conceptual diagram showing the state of the heat-sensitive odor-emitting component shown in FIG. 5 mounted on a heat generation site.
Figure 7:
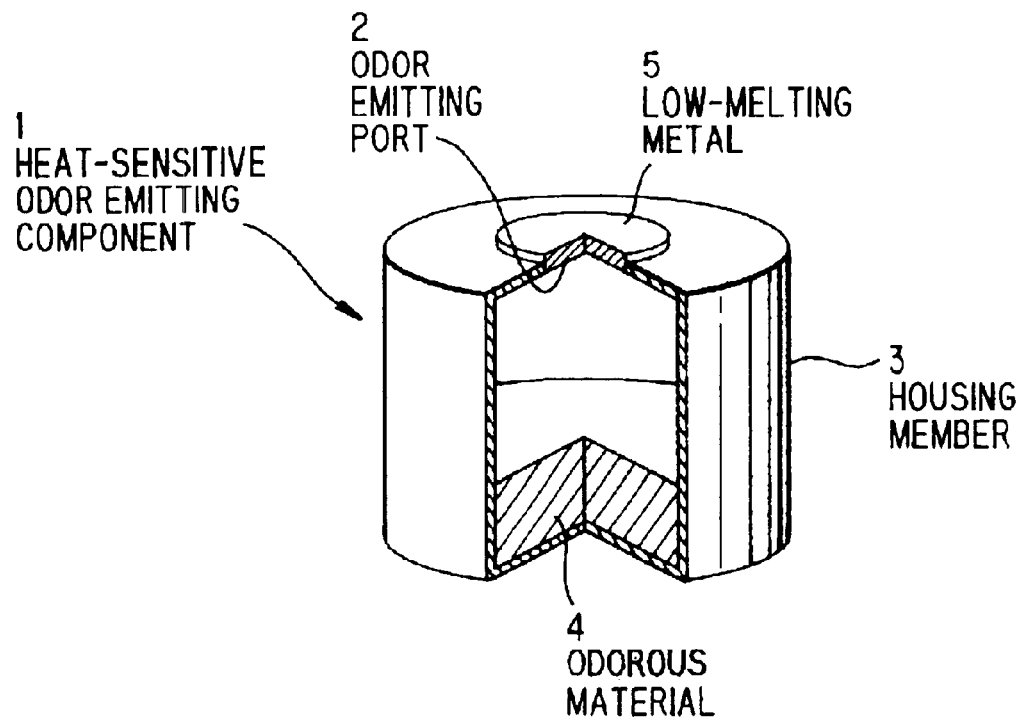
FIG. 7 is a partially broken perspective view showing a further preferred embodiment of the heat-sensitive odor-emitting component according to the first feature of the invention.

According to another preferred embodiment of the invention, the heat-sensitive odor-emitting component is in the form of a sheet as shown in FIG. 5. According to a further preferred embodiment of the invention, the heat-sensitive odor-emitting component is in the form of a can as shown in FIG. 7. The embodiment shown in FIG. 5 is advantageous in that the adoption of a bag-like material, produced by putting, on top of the other, composite films formed of a metal foil 8 and a polymeric film 9 or composite films formed of glass and a polymeric film, as the housing member 3 can impart flexibility to the housing member. In the embodiment shown in FIG. 5, for example, the odor-emitting component can also be adhered and mounted onto a heat generation site 7 having a curved adhesive face as shown in FIG. 6. In the embodiment shown in FIG. 7, the housing member 3 may be formed of a copper can and a odor-emitting port 2 provided at the top of the housing member 3 may be closed with a lid-like low-melting metal 5. In this case, the odor-emitting component can be produced at low cost and can be reutilized simply by replacing the low-melting metal 5 and the odorous material 4 contained in the housing member 3.

The use of ethyl alcohol or an aqueous ethyl alcohol solution as the odorous material permits a person or sensor near the odor-emitting component to surely sense the presence of the odorous material and, at the same time, can avoid an adverse effect on a person who has smelled the odorous material.

Second Feature of Invention

Preferred embodiments of the heat-sensitive odor-emitting component according to the second feature of the invention will be explained in conjunction with FIGS. 8 and 9.

Figure 8:
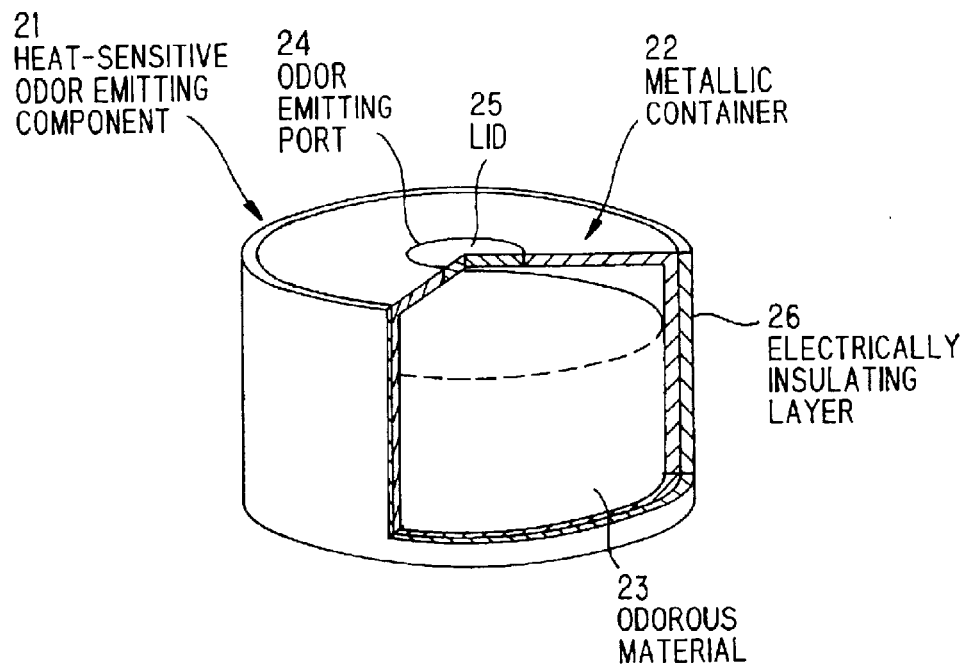
FIG. 8 is a partially broken perspective view showing a preferred embodiment of the heat-sensitive odor-emitting component according to the second feature of the invention.
Figure 9:
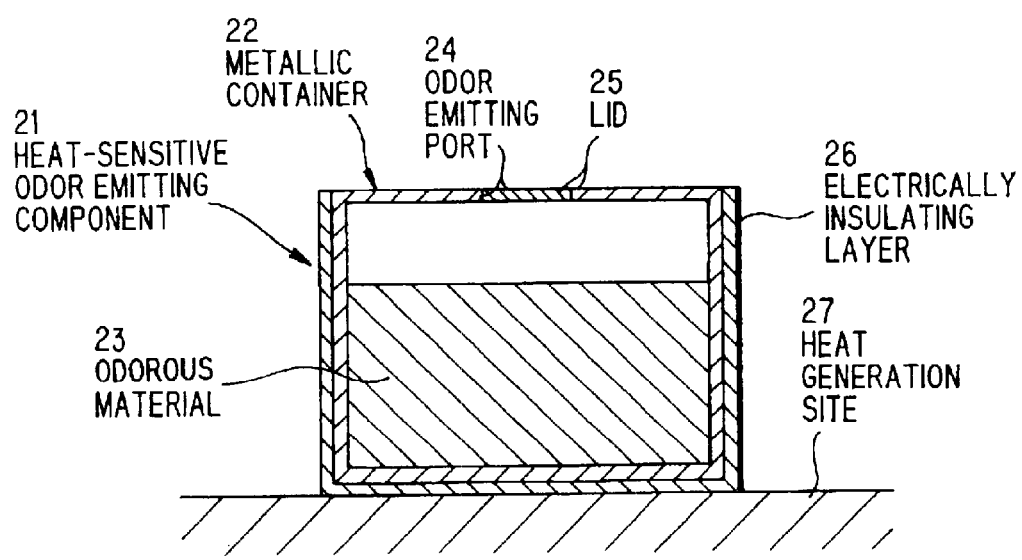
FIG. 9 is a cross-sectional view showing the state of the heat-sensitive odor-emitting component according to the second feature of the invention mounted on a heat generation site.

FIGS. 8 and 9 show a preferred embodiment of the heat-sensitive odor-emitting component according to the second feature of the invention.

As shown in the drawings, in a heat-sensitive odor-emitting component 21 according to this preferred embodiment according to the second feature of the invention, a circular odor-emitting port 24 is provided at the top of a can-like metallic container 22. An odorous material 23 is introduced into the metallic container 22 through the odor-emitting port 24. The odor-emitting port 23 is sealed with a low-melting metal lid 25, and the circumference of the metallic container 22 is covered with an electrically insulating layer 26.

Here the metallic container 22 is not particularly limited so far as the metallic container 22 is formed of a metal which at least has a melting point above the melting point of the low-melting metal lid 25 and is not easily attacked by the odorous material 23 contained in the metallic container 22.

Preferably, however, the metallic container 22 is formed of a metal, which is relatively low in cost and has corrosion resistance high enough to avoid the leakage of the odorous material 23 for a long period of time, for example, aluminum, an aluminum alloy, or stainless steel.

The lid 25 for sealing the odor-emitting port 24 of the metallic container 22 may be formed of any material without particular limitation so far as the metal has a melting point in a temperature region just below a temperature which possibly leads to accidents caused by overheating, troubles of equipment caused by overheating, and the like, for example, has a melting point in the range of 50 to 200° C. Specifically, metals, such as lead, tin, zinc, bismuth, and indium, or alloys of these metals are suitable, and a desired melting temperature can be properly set by selecting a metal from these metals or alloying these metals at a predetermined ratio. For example, indium per se has a melting point of about 156° C., and tin per se has a melting point of 232° C. On the other hand, alloying 52 parts by weight of indium with 48 parts by weight of tin provides a low-melting alloy having a melting point of 117° C. This indium-tin alloy is used for a heat generation site where a rise in temperature to above the temperature 117° C. possibly leads to accidents caused by overheating or troubles caused by overheating. The use of harmful metals, such as lead, is preferably avoided from the viewpoint of environmental contamination.

The odorous material 23 is a material that, upon heating, can be volatilized and detected by the sense of smell of human or by a gas detection sensor or the like. Examples thereof include: alcohols such as ethyl alcohol (ethanol), propanol, butanol, and phenol; saturated hydrocarbons such as methane, butane, and octane; unsaturated hydrocarbons such as ethylene, acetylene, butadiene, benzene, and naphthalene; ketones such as acetone, and methyl ethyl ketone; carboxylic acids such as formic acid, acetic acid, lactic acid, acrylic acid, and methacrylic acid; and esters such as methyl acetate and ethyl acetate. Among them, ethyl alcohol or an aqueous ethyl alcohol solution is optimal from the viewpoint of influence on the human body.

The electrically insulating layer 26 may be formed of any material without particular limitation so far as the material can surely cut off electricity which, upon the occurrence of shortcircuiting accident, flows across the metallic container 22. More specifically, for example, a cover or sheet of rubber, plastic or the like may be used. An electrically insulating layer formed by coating an electrically insulating coating material is advantageous in cost because the covering can be easily formed.

The heat-sensitive odor-emitting component 21 having the above construction in this preferred embodiment according to the second feature of the invention may be directly installed around a heat generation site 27 as a monitoring object, for example, a motor, an integrated circuit, or a distribution board, or may be applied and fixed directly to the heat generation site 27 with the aid of an adhesive as shown in FIG. 9. In this case, when the temperature of the heat generation site 27 is generally raised to above the operation temperature and is consequently brought to an overheated state, the heat is immediately conveyed to the whole metallic container 22. This causes the lid 5, with which the odor-emitting port 24 in the metallic container 22 has been sealed, to be immediately melted down to instantaneously open the odor-emitting port 24, whereby the odorous material 23 contained in the metallic container 22 is emitted at a time to the outside of the container 22.

By virtue of this construction, a person near the odor-emitting component perceives the occurrence of the phenomenon by the sense of smell of human. Alternatively, the presence of the odorous material 23 may be detected by a gas detection sensor which then sounds the alarm or carries out other means to advise the person of the overheating. Thus, the person can be surely learned directly or indirectly the fact that the heat generation site 27 as the monitoring object is in an overheated state and has a fear of the overheating causing an accident.

Even when overcurrent has flowed across the heat generation site 27 due to an shortcircuiting accident, since the surface of the metallic container 22 is covered with the electrically insulating layer 26, there is no fear that the current flowing across the heat generation site 27 reaches the metallic container 22. Therefore, troubles such as melting of the lid 25 and the leakage of the odorous material 23 can be surely avoided.

An experiment was carried out as follows. A plurality of heat-sensitive odor-emitting components 21 each in a form as shown in FIG. 8 were prepared using an aqueous ethyl alcohol solution as the odorous material 23 and using a low-melting metal having a melting point of 96° C. as the lid 25. The heat-sensitive odor-emitting components 21 were installed respectively at a plurality of places within a distribution board, and an odor sensor was provided to monitor the occurrence of an abnormal overheat phenomenon within the distribution board. As a result, only the heat-sensitive odor-emitting component 21, which was placed at a site intentionally heated to 100° C., worked, and this was sensed by the odor sensor. A current on a level, which is expected in a usual shortcircuiting accident, was allowed to flow to the installation sites. As a result, none of the heat-sensitive odor-emitting components 21 erroneously worked.

Third Feature of Invention

Preferred embodiments of the heat-sensitive odor-emitting component according to third feature of the invention will be explained in conjunction with FIGS. 10 and 11.

FIG. 10 is a preferred embodiment of the heat-sensitive odor-emitting component according to the third feature of the invention.

As shown in the drawing, in a heat-sensitive odor-emitting component 31, an odorous material 33 is contained in a can-like container 32, and an odor-emitting port 34 provided on the center of the top surface of the container is sealed with a low-melting sealing material 35.

The container 32, into which the odorous material 33 is sealed, is not particularly limited so far as the container 32 is formed of a material which permits the odorous material 33 to be stably contained in the container. In addition to inorganic materials such as metals, glass, and ceramics, organic materials such as plastics may be used. The use of a metal in a simple form or an alloy, which is particularly excellent in thermal conductivity and long-term stability, that is, a metallic container, is preferred from the viewpoint of properties required. The container 32 may also be in a capsule or box form and is not particularly limited.

The odorous material 33 sealed into the container 32 is not particularly limited so far as, upon heating, the material can be volatilized and easily detected by the sense of smell of human or by an electric gas detection sensor or the like. Examples of odorous materials usable herein include: alcohols such as ethanol, propanol, butanol, and phenol; saturated hydrocarbons such as methane, butane, and octane; unsaturated hydrocarbons such as ethylene, acetylene, butadiene, benzene, and naphthalene; ketones such as acetone, and methyl ethyl ketone; carboxylic acids such as formic acid, acetic acid, lactic acid, acrylic acid, and methacrylic acid; and esters such as methyl acetate and ethyl acetate. When an odor detector of a type, which attempts to detect the odorous material 33 through an oxidation reaction of an organic material, is also used, the use of the so-called "combustible material" such as ethanol, toluene, or xylene is preferred.

The sealing material 35 for covering the odor-emitting port 34 in the container 32 is a low-melting alloy (metal) which has a melting point below the melting point of the container 32 and just below a temperature region which possibly leads to an accident caused by overheating or trouble of the equipment caused by overheating, for example, a low-melting alloy having a melting point in the range of 60 to 180° C. Specifically, when the melting point is below 60° C., the difference between the temperature below 60° C. and room temperature is small. In this case, it is difficult to distinguish the abnormal overheated state from the normal state, and, in addition, it is difficult to produce an alloy having a melting point below 60° C. On the other hand, when the melting point is above 180° C., damage to equipment or the like as a monitoring object becomes significant. Further, in this case, the decomposition of the organic material used in the equipment or the like as the monitoring object proceeds, and the electric odor sensor is operated by the resultant decomposition gas, making it unnecessary to use the odor-emitting component according to the invention.

Specific examples of optimal low-melting alloys satisfying the above requirement include an indium-tin alloy, a tin-bismuth alloy, an indium-bismuth alloy, and an indium-tin-bismuth alloy. A low-melting alloy having any desired melting point can be easily produced by properly varying the alloying ratio. For example, in the case of the indium-tin alloy, when indium and tin are alloyed at a weight ratio of 34:66, the resultant alloy has a melting point of 72° C. In the case of the tin-bismuth alloy, when tin and bismuth are alloyed at a weight ratio of 48:52, the resultant alloy has a melting point of 117° C. In the case of the indium-bismuth alloy, when indium and bismuth are alloyed at a weight ratio of 58:42, the resultant alloy has a melting point of 136° C. Further, in the case of the indium-tin-bismuth alloy, when indium, tin, and bismuth are alloyed at a weight ratio of 48.2:44.4:7.4, the resultant alloy is a low-melting alloy having a melting point of 96° C.

In the invention, the odorous material 33 and the sealing material 35 are used in proper combination. In this combination, the difference between the boiling temperature of the odorous material 33 and the melting point of the sealing material 35 is within ±20° C. When the boiling point of the odorous material 33 is at least 20° C. below the melting point of the sealing material 35, an internal pressure is applied to the container 32 even though the boiling point is considerably below the melting point of the sealing material 35. In this case, the storage stability of the container 32 is significantly lowered, and, in some cases, the odorous material 33 is leaked, making it impossible for the odor-emitting component to normally function. On the other hand, when the boiling point of the odorous material 33 is at least 20° C. above the melting point of the sealing material 35, the storage stability can be ensured. In this case, however, the odor-emitting property (volatility of odor) is deteriorated, and the odor is less likely to be spread, making it difficult to detect the odor.

As shown in FIG. 11A, the heat-sensitive odor-emitting component 31 having the above construction in this preferred embodiment according to the third feature of the invention may be installed around a heat generation site 36 as a monitoring object, for example, a motor, an integrated circuit, or a distribution board, or may be applied and fixed directly to the heat generation site 36 with the aid of an adhesive. In this case, when the temperature of the heat generation site 36 is generally raised to above the usual operation temperature and, consequently, the heat generation site 36 is brought to an overheated state, as shown in FIG. 11B, the heat melts down the sealing material 35 to open the odor-emitting port 34 through which the odorous material 33 contained in the container is emitted to the outside of the container.

By virtue of this construction, a person near the odor-emitting component perceives the occurrence of the phenomenon by the sense of smell of the person. Alternatively, the presence of the released odorous material may be detected, for example, by a gas detection sensor which then sounds the alarm or carries out other means to advise the person of the overheating. Thus, the person can be surely learned directly or indirectly the fact that the heat generation site 36 as the monitoring object is in an overheated state and has a fear of the overheating causing an accident.

When the heat generation site 36 as the monitoring object is large or extends in a wide range, a plurality of heat-sensitive odor-emitting components 31 may be provided either together or at given intervals on the heat generation site 36. In this case, a site at which heat has been generated can be quickly and surely specified by pursuing the odor emission source.

The following examples further illustrate the third feature of the invention.

EXAMPLE 1

Ethanol having a boiling point of 79° C. was provided as an odorous material 33 and was placed in a metallic container 32 shown in FIG. 10. An odor-emitting port 34 was sealed with a sealing material 35 composed of a bismuth-indium alloy (weight ratio=34:66) having a melting point of 72° C. to prepare an odor-emitting component 31.

Thereafter, the odor-emitting component 31 was gradually heated. As a result, when the temperature reached about 75° C., the sealing material 35 melted down to open the odor-emitting port 34 through which ethanol was leaked. This increased the output of an electric odor detection sensor.

EXAMPLE 2

An odor-emitting component 31 was prepared in the same manner as in Example 1, except that n-heptane having a boiling point of 98° C. was used as the odorous material 33 and an indium-tin-bismuth alloy (weight ratio= 48.2:44.4:7.4) having a melting point of 96° C. was used as the sealing material 35.

Thereafter, the odor-emitting component 31 was gradually heated. As a result, when the temperature reached about 100° C., the sealing material 35 melted down to open the odor-emitting port 34 through which n-heptane was leaked. This increased the output of an electric odor detection sensor.

EXAMPLE 3

An odor-emitting component 31 was prepared in the same manner as in Example 1, except that toluene having a boiling point of 111° C. was used as the odorous material 33 and a tin-indium alloy (weight ratio=48:52) having a melting point of 117° C. was used as the sealing material 35.

Thereafter, the odor-emitting component 31 was gradually heated. As a result, when the temperature reached about 120° C., the sealing material 35 melted down to open the odor-emitting port 34 through which toluene was leaked. This increased the output of an electric odor detection sensor.

EXAMPLE 4

An odor-emitting component 31 was prepared in the same manner as in Example 1, except that o-xylene having a boiling point of 144° C. was used as the odorous material 33 and a bismuth-tin alloy (weight ratio=58:42) having a melting point of 139° C. was used as the sealing material 35.

Thereafter, the odor-emitting component 31 was gradually heated. As a result, when the temperature reached about 145° C., the sealing material 35 melted down to open the odor-emitting port 34 through which o-xylene was leaked. This increased the output of an electric odor detection sensor.

COMPARATIVE EXAMPLE 1

An odor-emitting component 31 was prepared in the same manner as in Example 1, except that o-xylene having a boiling point of 144° C. was used as the odorous material 33 and a bismuth-indium alloy (weight ratio=34:66) having a melting point of 72° C. was used as the sealing material 35.

Thereafter, the odor-emitting component 31 was gradually heated. As a result, when the temperature reached about 72° C., the sealing material 35 melted down to open the odor-emitting port 34. However, the amount of xylene volatilized was so small that the output of the electric odor detection sensor was much lower than those in the above examples and was on a level that made it difficult to detect the presence of xylene.

COMPARATIVE EXAMPLE 2

Five odor-emitting components 31 were prepared in the same manner as in Example 1, except that ethanol having a boiling point of 79° C. was used as the odorous material 33 and a bismuth-tin alloy (weight ratio=58:42) having a melting point of 139° C. was used as the sealing material 35.

Thereafter, the five odor-emitting components 31 were simultaneously gradually heated. As a result, when the temperature reached around about 120 to 135° C., the odor-emitting port 34 was broken, by the internal pressure, rather than the meltdown of the sealing material 35. This caused spouting of ethanol contained in the container, and all the odor-emitting components 31 unfavorably worked below the working temperature.

As described above, in the heat-sensitive odor-emitting component according to the first feature of the invention, at approximately the same time that the temperature around the odor-emitting component or the temperature of a heat generation site has reached a predetermined temperature, an odorous material is immediately released around the odor-emitting component. By virtue of this, the odor-emitting component is highly sensitive to temperature. Further, as compared with the prior art technique wherein a resin microcapsule or film or the like is used, the housing member for housing therein an odorous material in the odor-emitting component according to the invention is less likely to be deteriorated. Therefore, for example, advantageously, the odor-emitting component according to the invention is highly stably maintained for a long period of time.

In the heat-sensitive odor-emitting component according to the second feature of the invention, in addition to high sensitivity to temperature and long-term stability, an additional advantage can be attained wherein, since the circumference of the metallic container has been covered with an electrically insulating layer, erroneous working derived from a shortcircuiting accident can be surely avoided and, for example, high stability and reliability can be advantageously realized.

In the heat-sensitive odor-emitting component according to the third feature of the invention, since the difference between the boiling point of the odorous material and the melting point of the sealing material is within ±20° C., the odor-emitting component accurately works at a desired temperature. This can avoid troubles including that the odor-emitting component erroneously works before the temperature reaches an abnormal overheat temperature, or the odor-emitting component erroneously does not work even after the temperature reaches an abnormal overheat temperature. Thus, the odor-emitting component according to the invention is highly reliable.

The invention has been described in detail with particular reference to preferred embodiments, but it will be understood that variations and modifications can be effected within the scope of the invention as set forth in the appended claims.

What is claimed is:

1. A heat-sensitive odor-emitting component comprising:

a housing member composed mainly of an inorganic material;

at least one odor-emitting port provided in the housing member; and an odorous material contained in the housing member;

wherein the odorous material is a material that includes alcohols or ketones or both alcohols and ketones, and wherein the odor-emitting port is sealed with a metal having a low melting temperature.

2. The heat-sensitive odor-emitting component according to claim 1, wherein the housing member is formed of a metal foil or a composite film of a metal foil stacked on a polymeric film.

3. The heat-sensitive odor-emitting component according to claim 2, wherein an adhesive is coated onto the surface of the housing member to fix the housing member to a heat generation portion.

4. The heat-sensitive odor-emitting component according to claim 1, wherein the housing member is formed of glass or a glass-coated polymeric film.

5. The heat-sensitive odor-emitting component according to claim 4, wherein an adhesive is coated onto the surface of the housing member to fix the housing member to a heat generation portion.

6. The heat-sensitive odor-emitting component according to claim 1, wherein the housing member is formed of a metallic container.

7. The heat-sensitive odor-emitting component according to claim 6, wherein an adhesive is coated onto the surface of the housing member to fix the housing member to a heat generation portion.

8. The heat-sensitive odor-emitting component according to claim 1, wherein an adhesive is coated onto the surface of the housing member to fix the housing member to a heat generation portion.

9. The heat-sensitive odor-emitting component according to claim 8, wherein an adhesive is coated onto the surface of the housing member to fix the housing member to a heat generation portion.

10. A heat-sensitive odor-emitting component comprising:
- a container composed mainly of an inorganic material;
- at least one odor-emitting port provided in the container; and
- an odorous material contained in the container;
- wherein the odor-emitting port is sealed with a sealant;
- wherein the odorous material is a material that includes alcohols or ketones;
- wherein the sealant melts at a predetermined temperature to open the odorous material; and
- wherein the difference between the melting point of the sealant and the boiling point of the odorous material is within ±20° C.

11. The heat-sensitive odor-emitting component according to claim 10, wherein the odorous material is a combustible material.

12. The heat-sensitive odor-emitting component according to claim 11, wherein the sealant is formed of an alloy having a lower melting point than the container.

13. The heat-sensitive odor-emitting component according to claim 10, wherein the sealant is formed of an alloy having a lower melting point than the container.

14. The heat-sensitive odor-emitting component according to claim 13, wherein the low-melting alloy is an indium-tin alloy, a tin-bismuth alloy, an indium-bismuth alloy, or an indium-tin-bismuth alloy.

15. The heat-sensitive odor-emitting component according to claim 13, wherein the low-melting alloy is an indium-tin alloy comprised of indium and tin at a weight ratio of 34:66, a tin-bismuth alloy comprised of tin and bismuth at a weight ratio of 48:52, an indium-bismuth alloy comprised of indium and bismuth at a weight ratio of 58:42, or an indium-tin-bismuth alloy comprised of indium, tin, and bismuth at a weight ratio of 48.2:44.4:7.4.

16. The heat-sensitive odor-emitting component according to claim 13, wherein the low-melting alloy has a melting point of 60 to 180° C.

17. The heat-sensitive odor-emitting component according to claim 16, wherein the low-melting alloy is an indium-tin alloy, a tin-bismuth alloy, an indium-bismuth alloy, or an indium-tin-bismuth alloy.

18. The heat-sensitive odor-emitting component according to claim 16, wherein the low-melting alloy is an indium-tin alloy comprised of indium and tin at a weight ratio of 34:66, a tin-bismuth alloy comprised of tin and bismuth at a weight ratio of 48:52, an indium-bismuth alloy comprised of indium and bismuth at a weight ratio of 58:42, or an indium-tin-bismuth alloy comprised of indium, tin, and bismuth at a weight ratio of 48.2:44.4:7.4.

* * * * *